United States Patent
Doye et al.

(10) Patent No.: US 9,492,812 B2
(45) Date of Patent: Nov. 15, 2016

(54) COMPONENT WITH AN ANTIMICROBIAL SURFACE AND USE THEREOF

(75) Inventors: Christian Doye, Berlin (DE); Ursus Krüger, Berlin (DE); Uwe Pyritz, Berlin (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 791 days.

(21) Appl. No.: 12/998,719

(22) PCT Filed: Nov. 20, 2009

(86) PCT No.: PCT/EP2009/065540
§ 371 (c)(1),
(2), (4) Date: May 24, 2011

(87) PCT Pub. No.: WO2010/057969
PCT Pub. Date: May 27, 2010

(65) Prior Publication Data
US 2011/0229728 A1    Sep. 22, 2011

(30) Foreign Application Priority Data
Nov. 24, 2008 (DE) .................. 10 2008 059 164

(51) Int. Cl.
| | | |
|---|---|---|
| *B32B 15/04* | (2006.01) | |
| *B01J 23/68* | (2006.01) | |
| *A01N 59/16* | (2006.01) | |
| *B01J 23/889* | (2006.01) | |
| *B01J 37/02* | (2006.01) | |

(52) U.S. Cl.
CPC .............. *B01J 23/688* (2013.01); *A01N 59/16* (2013.01); *B01J 23/8892* (2013.01); *B01J 37/0225* (2013.01)

(58) Field of Classification Search
None
See application file for complete search history.

(56) References Cited

U.S. PATENT DOCUMENTS

| | | | | |
|---|---|---|---|---|
| 4,172,183 A | * | 10/1979 | Ruetschi ....................... | 429/128 |
| 5,120,423 A | * | 6/1992 | Kurita et al. ................. | 205/200 |
| 7,223,715 B2 | * | 5/2007 | Terashima et al. ........... | 502/339 |
| 7,648,799 B2 | * | 1/2010 | Huang et al. ................. | 429/206 |
| 2003/0078161 A1 | * | 4/2003 | Terashima et al. ........... | 502/325 |

FOREIGN PATENT DOCUMENTS

| | | |
|---|---|---|
| CN | 1843995 | 10/2006 |
| CN | 101037327 | 9/2007 |
| DE | 102008059164.5 | 11/2008 |
| JP | 63-21751 | 1/1988 |
| JP | 5-203336 | 8/1993 |

(Continued)

OTHER PUBLICATIONS

Chou et al. J of Power Sources. 162 (2006), 727-734.*

(Continued)

*Primary Examiner* — Vera Katz
(74) *Attorney, Agent, or Firm* — Slayden Grubert Beard PLLC

(57) ABSTRACT

The surface of a component includes metallic fractions of Ag and/or Ni, touching $MnO_2$ fractions which provide an antimicrobial effect. When using toxicologically safe Ni, these antimicrobial surfaces can be used in the food industry, for example. The surface can, for example, be applied by way of a coating on the component with the metallic fraction and the $MnO_2$ fraction applied in two layers.

12 Claims, 2 Drawing Sheets

(56) References Cited

FOREIGN PATENT DOCUMENTS

| JP | 9-77620 | 3/1997 |
|---|---|---|
| JP | 2001-152129 | 6/2001 |
| SU | 1725921 A1 | 4/1992 |
| WO | 01/11955 A2 | 2/2001 |
| WO | 2006/050477 A2 | 5/2006 |

OTHER PUBLICATIONS

Chinese Office Action issued Sep. 20, 2012 in corresponding Chinese Patent Application No. 200980147357.X.

German Office Action for Application No. 10 2008 059 164.5-45; dated May 19, 2009.

International Search Report for Application No. PCT/EP2009/065540; mailed Mar. 17, 2010.

Office Action issued Jul. 8, 2013 in corresponding Russian Application No. 2011125930.

Chinese Office Action for corresponding Chinese Application No. 200980147357.X; Issued May 24, 2013.

Russian Office Action mailed Feb. 20, 2014 in corresponding Russian Application No. 2011125930.

Office Action issued May 22, 2014 in corresponding Chinese Patent Application No. 200980147357.X.

\* cited by examiner

COMPONENT WITH AN ANTIMICROBIAL SURFACE AND USE THEREOF

CROSS REFERENCE TO RELATED APPLICATIONS

This application is the U.S. national stage of International Application No. PCT/EP2009/065540, filed Nov. 20, 2009 and claims the benefit thereof. The International Application claims the benefits of German Application No. 10 2008 059 164.5 filed on Nov. 24, 2008, both applications are incorporated by reference herein in their entirety.

BACKGROUND

Described below are components with an antimicrobial surface and to a method for use thereof. It is generally known from the related art to mix different substances together in order to generate an antimicrobial effect. These substances are also potentially suitable for processing in a coating for a component. For example, JP 2001-152129 A discloses a powder mixture which, among other things, also contains MgO and Ni. Mixing together a large number of different substances is intended to achieve an antimicrobial action for the widest possible spectrum of microorganisms (cf. also Derwent Abstract for JP 2001-152129 A). The powder can therefore be used to combat microorganisms. Combat is to be understood in the broad sense as suppressing the multiplication of the microorganisms, killing the microorganisms or inactivating them, i.e. preventing them from exerting a possibly harmful effect. In addition to microorganisms such as viruses and bacteria, an antimicrobial action in respect of fungi can also be achieved.

However, the large number of the substances according to JP 2001-152129 A makes it difficult to predict the specific antimicrobial effects. Moreover, although a mixture of antimicrobial substances covers a broader spectrum, this may mean that its action is not so strong. It is therefore desirable to make available a component, and a use thereof, having a relatively simply configured antimicrobial surface and a relatively strong antimicrobial action.

According to WO 2006/050477 A2, it is known that surfaces with an antimicrobial action can be used, for example, to keep drinking water free of germs. As antimicrobial components, it is proposed to use transition metals, oxides of transition metals, salts of transition metals, or combinations of these substances. The transition metals also include manganese, silver and nickel and, as the oxide of a transition metal, also manganese oxide. A larger number of active substances can be used simultaneously to achieve a broad-spectrum action on different microorganisms.

SUMMARY

This is achieved, with the component mentioned at the outset, by virtue of the fact that this surface includes metallic fractions (or portions) and, touching the latter, $MnO_2$ fractions (or portions), wherein the metallic fraction may be Ag and/or Ni. In testing different substance pairings of a metal and of a ceramic, it has surprisingly been found that a pairing of $MnO_2$ with Ag and/or Ni has a particularly strong antimicrobial action. In this way, components with antimicrobial layers can be produced in a relatively simple way, and, because of the relatively few antimicrobial substances used, it is easier to predict the effect of these components and their compatibility with other components in the particular case of use.

The surface of the component does not have to be completely covered with the metallic fractions and the $MnO_2$ fractions. A partial coating is already sufficient to achieve the antimicrobial action. Depending on the particular use, the size of this coating is to be chosen such that the available antimicrobial surface is sufficient for the desired effect of combating microorganisms and/or fungi. The $MnO_2$ fraction in relation to the overall surface formed by both fractions should be at least 10%, such as 30 to 70%, in particular 50%.

Provision is also made that the $MnO_2$ is present at least partially in the γ modification. The γ modification is a structural configuration of the crystal formed by the $MnO_2$ that advantageously has a strong catalytic action. However, the real structure of the $MnO_2$ does not lie exclusively in the γ modification but in part also in other modifications (e.g. in the β modification of $MnO_2$). However, according to a particular embodiment, the structural fraction of the $MnO_2$ present in the γ modification should be more than 50% by weight.

According to another embodiment, provision is made that the component is formed of the metal providing the metallic fraction of the antimicrobial surface, and an only partially covering layer of $MnO_2$ is applied to this component. These are components made of Ag or Ni which, because of their material composition, already provide one constituent required for the production of the antimicrobial surface. The surface can be produced in a particularly advantageously simple way on these components, by applying a non-covering layer of the other fraction of the surface, namely $MnO_2$.

Conversely, it is also conceivable that the component is formed of ceramic providing the $MnO_2$ fraction of the antimicrobial surface, and an only partially covering layer of the metal is applied to this component. For example, the component could be designed as a ceramic component subject to wear. This ceramic component also does not have to consist exclusively of $MnO_2$. For example, it is conceivable that the ceramic is produced as sintered ceramic from different types of particles, with $MnO_2$ representing one type of the particles. In this variant, however, it should be noted that the processing temperature for the component must be below 535° C., since $MnO_2$ is converted to MnO at this temperature and, consequently, loses its excellent antimicrobial properties in the material pairing.

According to another embodiment, provision is made that the component has a coating, which provides the metallic fractions and the $MnO_2$ fractions of the surface. In this variant, components of different materials can be coated, in which case the antimicrobial properties of the layer are advantageously obtained solely through the nature of the layer or of the antimicrobial surface formed by the latter. A suitable coating method must in each case be chosen for the particular material of the component.

As a method for producing the layer on the component, it is possible, for example, to use cold-gas spraying in which the antimicrobial surface is generated by spraying $MnO_2$ particles. The $MnO_2$ forms only fractions of the antimicrobial surface, and the metallic fractions are formed by Ni and/or Ag. As has already been described, the metallic fractions can either be provided by the component itself or are added as particles to the cold-gas stream, such that the metallic fractions of the surface are formed by the developing layer.

It is also possible in particular to use $MnO_2$ particles that have only partially the γ modification of the $MnO_2$ structure. In this case, the cold-gas spraying has to be carried out at operating temperatures below the decomposition temperature of the γ modification. This temperature is 535° C. When choosing the temperature of the cold-gas stream, a certain safety interval in relation to this decomposition temperature can be maintained. It has been found, however, that if this temperature is briefly exceeded when the $MnO_2$ particles strike the surface, this has no effect on the structure, because this temperature increase occurs only extremely locally in the surface area of the processed $MnO_2$ particles. The respective core of the particles, which core remains in an uncritical temperature range, appears to be able to sufficiently stabilize the γ modification of the particle structure, such that the γ modification of the $MnO_2$ structure is also maintained on the antimicrobially active surface of the particles.

Moreover, heating the $MnO_2$ to over 450° C. leads to conversion of the $MnO_2$ to $Mn_2O_3$. This process, however, takes place only slowly, such that briefly exceeding the temperature, as happens in cold-gas spraying, does not cause any damage.

In order to maintain the excellent antimicrobial properties of the $MnO_2$, the γ modification of the structure must be contained at least partially in the $MnO_2$ particles. This can be achieved by mixing the $MnO_2$ particles with manganese oxide particles of other modifications. Another possibility is that the particles contain phase mixtures, such that the γ modification of the $MnO_2$ is not the only one present in the particles.

It is also advantageous if nanoparticles with a diameter of >100 nm are processed as $MnO_2$ particles. Nanoparticles within this specification are to be understood as particles that have a diameter of <1 μm. It has in fact been surprisingly found that such small particles of $MnO_2$ can be deposited on the antimicrobial surface with high efficacy of deposition. It is normally assumed, by contrast, that particles of less than 5 μm cannot be deposited by cold-gas spraying, since the low mass of these particles means that the kinetic energy imparted by the cold-gas stream is insufficient for deposition. It has not been possible to establish the reason why this does not apply specifically to $MnO_2$ particles. In addition to the effect of the kinetic deformation, it would appear that other adherence mechanisms are also at play in the process of layer formation.

The processing of $MnO_2$ nanoparticles has the advantage that, with relatively little material, it is possible to achieve a relatively large specific surface area and, as a result, a pronounced increase in the antimicrobial action. The boundary lines between the $MnO_2$ fractions and metallic fractions of the antimicrobial surface are also advantageously greatly lengthened in this way, which also results in a pronounced increase in the antimicrobial properties.

It is advantageous if a mixture of $MnO_2$ particles and metallic particles is used for the metallic fractions of the antimicrobial surface, that is to say Ni and/or Ag. In particular, by a suitable choice of temperature and particle speed in the cold-gas stream, the energy input into the particles can be controlled in such a way that the specific (or inner) surface of the produced layer forming the antimicrobial surface is controlled. By having a higher porosity in the produced layer, the inner surface can be enlarged to make available an enlarged antimicrobial surface. In this way, the antimicrobial action can be increased. By contrast, however, it can also be advantageous if the surface is as smooth as possible, in order to counteract a tendency to soiling.

In addition to deposition by cold-gas spraying, other production methods are of course also conceivable. For example, the antimicrobial surface can be produced electrochemically. In this case, the metallic fraction of the antimicrobial surface is deposited as a layer electrochemically from an electrolyte in which particles of $MnO_2$ are suspended. During the electro-chemical deposition process, these particles are then incorporated in the developing layer and thus also form an $MnO_2$ fraction on the surface of the layer.

Another method is possible in which the layer is produced from a ceramic containing at least $MnO_2$. For this purpose, a mixture of pre-ceramic polymers, which form precursors of the desired ceramic, and metal particles can be applied in a solution to the component that is to be coated. The solvent is first evaporated, followed by conversion to the ceramic by heat treatment, such as below the decomposition temperature of the γ modification of $MnO_2$ (535° C.). If the temperature remains below 450° C., this will prevent the formation of $Mn_2O_3$.

With the methods, it is also possible to realize, among others, the following embodiments of the component. Thus, the produced coating can include a metallic layer to which an only partially covering layer of $MnO_2$ is applied. The metallic layer thus forms the metallic fraction of the surface that appears where the layer of $MnO_2$ is not covered. In this design of the component, it is advantageous that only a very small fraction of $MnO_2$ is needed. It is also conceivable for the abovementioned production methods to be used in combination.

Another possibility is that the coating includes a ceramic layer which provides the $MnO_2$ fraction and to which an only partially covering metallic layer is applied. This design of the component is important when the properties of the ceramic layer are of advantage for the component from the point of view of construction (for example for protection against corrosion).

It is also possible that the coating is formed of a ceramic which provides the $MnO_2$ fraction and in which metallic particles are embedded. This is particularly advantageous if the ceramic layer is subject to wear and if, in the event of continuing wear, i.e. removal of the layer, it is intended to maintain its antimicrobial properties. This is ensured by the fact that, upon removal of the ceramic layer, more and more $MnO_2$ particles are exposed, which guarantee the $MnO_2$ fraction on the surface. It is of course also conceivable that the layer includes a metallic matrix in which the particles of $MnO_2$ are embedded. For this layer too, the argument applies to the effect that the antimicrobial properties of the layer are maintained as it is removed.

The component can also be designed such that the component or a layer applied thereto is a material different from the metallic fraction and from $MnO_2$, and particles are present in and/or on the material (when subject to wear, see above), which particles each provide the metallic fractions and the $MnO_2$ fractions on their surface (meaning the surface of the particles). These are advantageously tailor-made particles that have antimicrobial properties and that can be introduced universally onto any surface or into any matrix. The method must be chosen that is suitable in each case for the introduction or application. For example, components made of plastic can also be produced with antimicrobial properties. The particles introduced into the layer or the component are either exposed when subject to wear or, if the component has a porous structure, can also be involved in the antimicrobial action if they form the walls of the pores.

It is particularly advantageous if the component has a surface that has low wettability. This surface is suitable for components that are intended to have self-cleaning properties, for example because they are exposed to weathering. It has been found that self-cleaning properties, which depend greatly on the low wettability of the surface, are reduced if microorganisms colonize this surface. This can be prevented by an antimicrobial action of this surface, such that the self-cleaning effect is advantageously maintained over a long period of time.

Finally, the above-described component may be used for combating microorganisms and/or fungi that come into contact with the component. The statements made above also apply to the use of the component.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
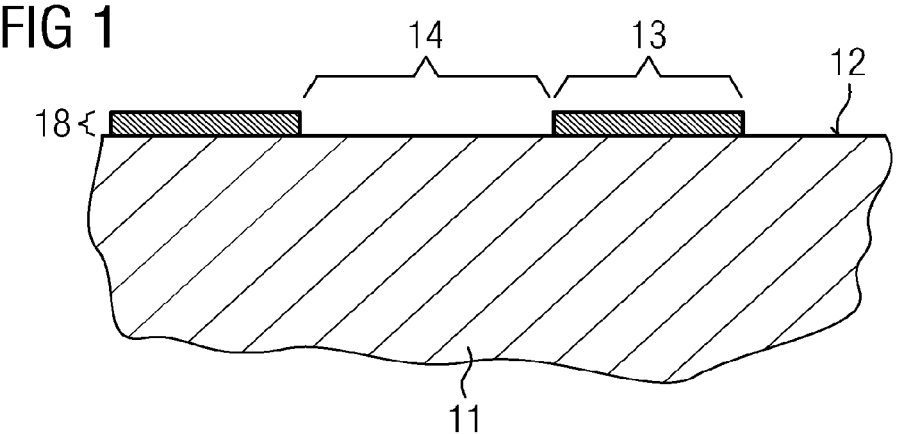
FIG. 1 is a cross-section of a component of Ni or Ag with islands of $MnO_2$.

Further details are described below with reference to the drawing. Identical or corresponding elements in the drawing are provided with the same reference signs in the individual figures and are explained more than once only insofar as there are differences between the individual figures. FIGS. 1 to 5 show different illustrative embodiments of the component with different antimicrobial surfaces.

FIGS. 1 to 5 each show a component 11 with a surface 12 that has antimicrobial properties. These properties are brought about by the fact that the surface in each case includes a fraction 13 of $MnO_2$, and, furthermore, a metallic fraction 14 of Ag or Ni is also provided.

However, there are differences as regards the structure of the components 11, which structure is in each case shown in cross section. The component according to FIG. 1 is formed of Ni or Ag, such that the surface 12 thereof automatically provides the metallic fraction 14. Moreover, islands of $MnO_2$ are formed on the surface 12 and provide the fraction 13. These can be applied, for example, as a non-covering coating by cold-gas spraying.

Figure 2:
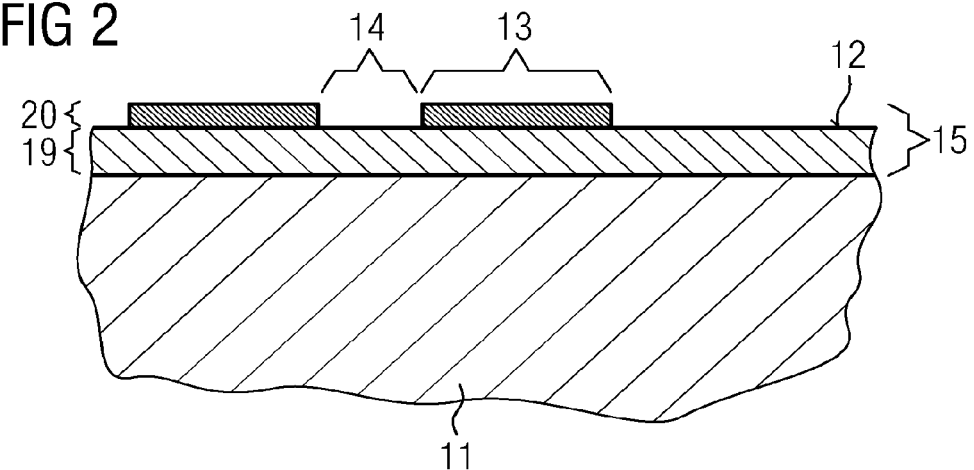
FIG. 2 is a cross-section of a component of a material without antimicrobial properties, covered by a layer of Ni or Ag having islands of $MnO_2$ formed thereon.

FIG. 2 shows a component 11 that is made of a material unsuitable for generating the antimicrobial properties of the surface. Therefore, a metallic layer 15 of Ni or Ag is applied to this component 11. Onto this layer, which provides the fraction 14, $MnO_2$ is applied in the manner described with reference to FIG. 1, such that fractions 13 are also obtained.

Figure 3:
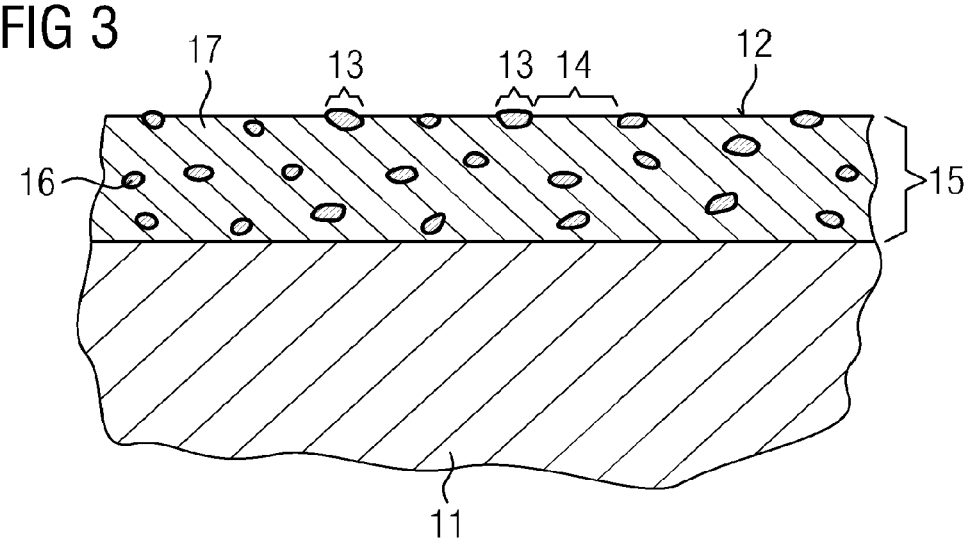
FIG. 3 is a cross-section of a component of a material without antimicrobial properties, covered by a layer of Ni or Ag doped with particles of $MnO_2$.

FIG. 3 shows that the metallic layer can also be doped with particles 16 of $MnO_2$, i.e. that these particles are located in the metallic matrix 17 of the metallic layer 15. To this extent they also form the part of the surface 12 that provides the fraction 13. The rest of the surface forms the fraction 14.

Figure 4:
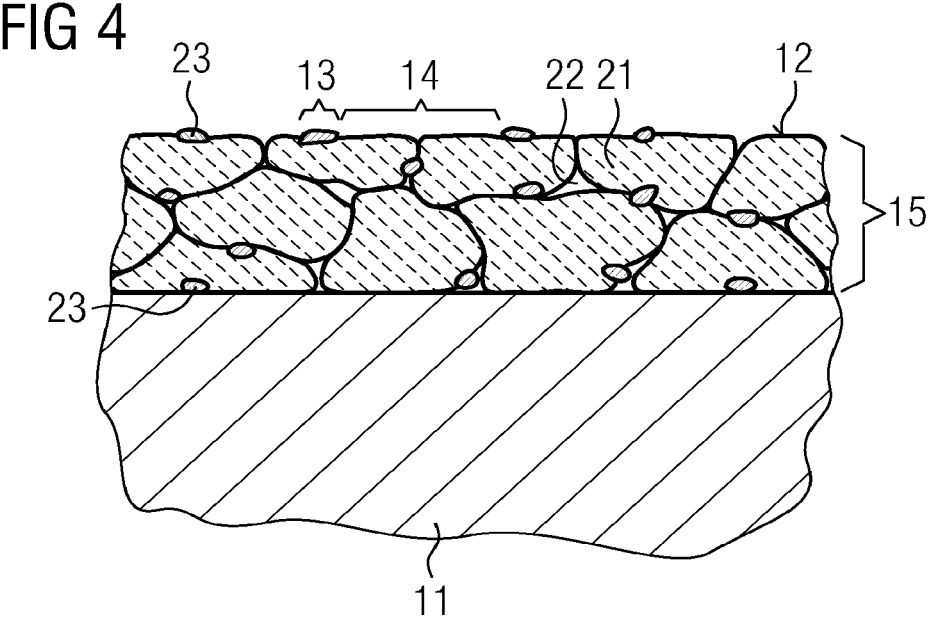
FIG. 4 is a cross-section of a component of a material without antimicrobial properties, with a coating formed by a ceramic matrix containing pores and metallic particles.

In FIG. 4, the coating 15 is formed by a ceramic matrix 21, the latter having pores 22 that increase the inner surface compared to the outer surface 12 of the component and thus also strengthen an antimicrobial effect. In the ceramic matrix 21, metallic particles 23 are provided which, on the surface 12, provide the fraction 13 and which also, in the pores, can exert an antimicrobial effect. As is also the case in FIG. 2 and FIG. 3, the component 11 according to FIG. 4 can be made of any desired material, it is necessary only to ensure that the coating 15 adheres to the component 11.

Figure 5:
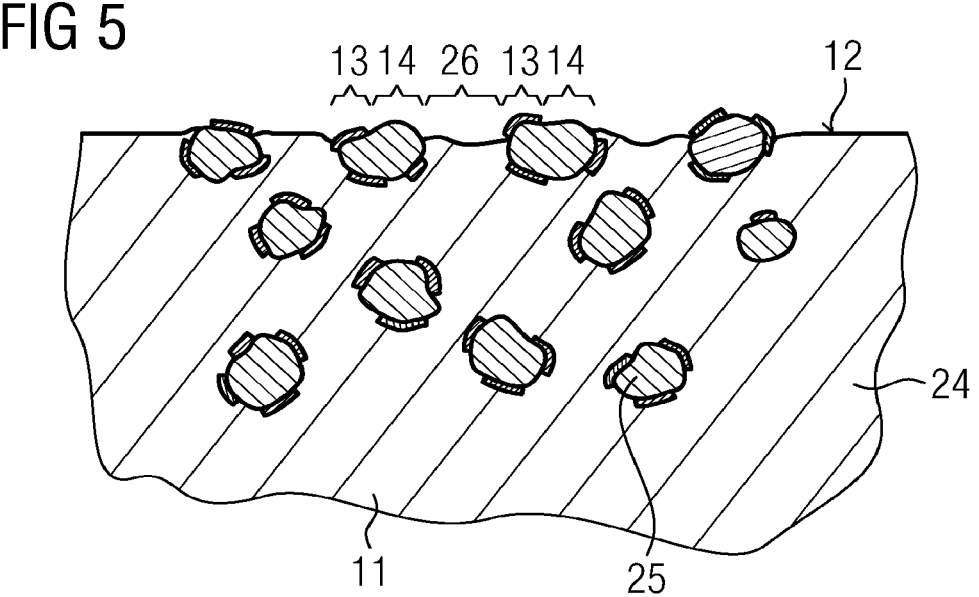
FIG. 5 is a cross-section of a component formed by a matrix of any material, such as plastic, with particles having surfaces with metallic fractions of Ni or Ag and $MnO_2$.

The component 11 according to FIG. 5 includes a matrix made of any desired material 24, e.g. plastic. Particles 25 are introduced into this matrix, the surface of each of these particles having metallic fractions of Ni or Ag and also fractions of $MnO_2$. In the illustrative embodiment according to FIG. 5, the particles themselves are formed of the metal, and the ceramic fractions are formed on the surface of the particles. The reverse configuration is of course also conceivable. Some of the particles lie exposed on the surface 12 of the component 11, as a result of which the metallic fractions 14 and the $MnO_2$ fractions 13 are formed 13. There are also fractions 26 of the surface 26 made of plastic that have no antimicrobial action. The ratio of the fractions mentioned can be influenced directly by the degree of filling of particles 25 in the material 24.

The table below shows the antimicrobial properties achieved by various surface samples. The following surfaces were examined in tests. A pure Ni surface, a surface formed from Ni and Pd, a surface with Ni and $MnO_2$, as further reference a surface formed of Ni, Pd and $MnO_2$, and, finally, a surface formed of Ag and $MnO_2$. The reference surfaces with Pd were examined for the reason that a strong antimicrobial action is ascribed to this material on its own and in combination with Ag. The pure Ni surface was examined in order to obtain a reference value for the antimicrobial action of this metal per se. The antimicrobial action of Ag and Ag/Pd is generally known and has also been proven, for which reason no such sample was tested.

The surfaces tested were generated by producing layers using cold-gas spraying. Depending on the desired surface composition, suitable powder mixtures were sprayed on. It was found that $MnO_2$ in particular could be processed in unexpectedly high concentrations, such that a relatively large fraction of $MnO_2$ on the surface was achievable.

To demonstrate the antimicrobial action, the surfaces were colonized by bacterial cultures of *Escherichia coli* and *Staphylococcus aureus*. The materials were tested according to ASTM E 2180-01. The test microbes were incubated for 30 minutes or 4 hours on the relevant surfaces before determination of the viable microbes. The test surfaces were stored at 20° C. during the tests. The test microbes were suspended, and the suspension contained a microbe count of between $10^6$ and $10^7$ per ml. The test surfaces were contaminated by application in each case of 0.5 ml of the microbe suspension, which were stored horizontally for the duration of the test. The number of microbes that could be recovered was determined after different times, specifically after 30 minutes and after 4 hours. To determine the number of colony-forming units (CFU), the residual microbes removed from the samples were incubated. The number of CFU recovered was compared to the microbes originally present arithmetically on the whole test surface, such that the percentage value shown in the table is an indicator of the amount of still viable microbes remaining.

| | Escherichia coli | | | | |
|---|---|---|---|---|---|
| Incubation time | Ni | Ni + Pd | Ni + MnO$_2$ | Ni + MnO$_2$ + Pd | Ag + MnO$_2$ |
| 30 min | 18.9% | 23.3% | 2.3% | 15.2% | 1.4% |
| 4 hours | 3.0% | <0.1% | <0.1% | <0.1% | <0.1% |

| | Staphylococcus aureus | | | | |
|---|---|---|---|---|---|
| Incubation time | Ni | Ni + Pd | Ni + MnO$_2$ | Ni + MnO$_2$ + Pd | Ag + MnO$_2$ |
| 30 min | 18.0% | 36.3% | 1.3% | 31.7% | 7.7% |
| 4 hours | 7.9% | 0.1% | <0.1% | <0.1% | <0.1% |

A comparison of the test results as shown in the table shows the following. The surfaces consisting only of Ni and MnO$_2$ or of Ag and MnO$_2$ show by far the strongest antimicrobial properties, which is confirmed in particular by the values after 30 minutes. Therefore, the microbicidal action is not only virtually complete, it also takes place rapidly. It has also been shown that the pairing of Ni and MnO$_2$ is not inferior to the pairing of Ag and MnO$_2$, although Ni on its own, unlike Ag on its own, does not have excellent antimicrobial properties.

This has the advantage that, instead of the silver that is often used for microbicidal purposes, it is possible to use the physiologically entirely safe Ni. This makes the surfaces available also for applications in the food industry for example, which has refrained from using silver ions because of silver-containing surfaces.

It will also be seen that it is not possible to generate the antimicrobial action using any pairings of MnO$_2$ with metals. As is shown by the example of Ni+Pd and also by the example of Ni+Pd+MnO$_2$, the antimicrobial action is reduced by the presence of Pd, and this has to be taken into account in generating antimicrobial surfaces. In such a case, a metallic component whose own surface impairs the antimicrobial properties of the Ni—MnO$_2$ or Ag—MnO$_2$ systems should be covered completely by a layer that provides the antimicrobial surface.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A component, comprising:
a component body with an antimicrobial surface, the antimicrobial surface including metallic portions touching MnO$_2$ portions, the metallic portions being formed from at least one of silver and nickel, and the MnO$_2$ portions at least partially having γ modification of MnO$_2$ with manganese oxide therein.

2. The component as claimed in claim 1, wherein a structural portion of the MnO$_2$ in the γ modification makes up more than 50% by weight of the MnO$_2$.

3. The component as claimed in claim 2,
wherein the component body is formed of a metal providing the metallic portions of the antimicrobial surface, and
wherein the MnO$_2$ portions are from an only partially covering layer of MnO$_2$ applied to the metal of the component body.

4. The component as claimed in claim 2,
wherein the component body is formed of a ceramic providing the MnO$_2$ portions of the antimicrobial surface, and
wherein the metallic portions are from an only partially covering layer of a metal applied to the ceramic of the component body.

5. The component as claimed in claim 2, wherein the antimicrobial surface is formed by a coating which provides the metallic portions and the MnO$_2$ portions.

6. The component as claimed in claim 4, wherein the coating comprises a metallic layer with an only partially covering layer of MnO$_2$.

7. The component as claimed in claim 4, wherein the coating comprises:
a ceramic layer providing the MnO2 portions; and
a metallic layer only partially covering the ceramic layer.

8. The component as claimed in claim 4, wherein the coating is a ceramic providing the MnO$_2$ portions and in which metallic particles are embedded.

9. The component as claimed in claim 4, wherein the coating is a metallic matrix in which particles of MnO$_2$ are embedded.

10. The component as claimed in claim 1, wherein the component body comprises:
a material different from the metallic portions and from MnO$_2$, and
particles, at least one of embedded in and coated on the material, providing the antimicrobial surface including the metallic portions and the MnO$_2$ portions.

11. The component as claimed in claim 1, further comprising a layer formed on the component body, of a material different from the metallic portions and from MnO$_2$, with particles, at least one of embedded in and coated on the material, providing the antimicrobial surface including the metallic portions and the MnO$_2$ portions.

12. The component as claimed in claim 1, wherein the antimicrobial surface has low wettability.

* * * * *